US00PP25047P3

(12) United States Plant Patent
Harris

(10) Patent No.: US PP25,047 P3
(45) Date of Patent: Nov. 11, 2014

(54) AZALEA PLANT NAMED 'MNIHAR028'

(50) Latin Name: ***Rhododendron* sp.**
Varietal Denomination: MNIHAR028

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 183 days.

(21) Appl. No.: 13/573,132

(22) Filed: Aug. 24, 2012

(65) Prior Publication Data

US 2014/0059729 P1 Feb. 27, 2014

(51) Int. Cl.
*A01H 5/00* (2006.01)

(52) U.S. Cl.
USPC ..... Plt./240

(58) Field of Classification Search
CPC ..... A01H 5/02
USPC ..... Plt./240
See application file for complete search history.

*Primary Examiner* — June Hwu
(74) *Attorney, Agent, or Firm* — Jondle Plant Sciences Division of Swanson & Bratschun, L.L.C.

(57) ABSTRACT

A new and distinct variety of azalea plant with spring and fall blooming, attractive, showy, single red flowers, easily propagated by semi-hardwood cuttings in late spring through summer, moderate growth rate under normal fertilization and moisture conditions; compact, uprightly rounded and freely-branching growth habit, grows well in containers, thrives in shade or sun and is hardy to Zone 7, is disclosed.

2 Drawing Sheets

Genus and species: *Rhododendron* sp.
Variety denomination: 'MNIHAR028'.

BACKGROUND OF THE NEW PLANT

The present invention is a new and distinct variety of evergreen azalea in the genus *Rhododendron*. This new azalea, hereinafter referred to as 'MNIHAR028', originated from a planned cross hybridization in a controlled environment in Lawrenceville, Ga. The parental records of 'MNIHAR028' are unavailable. The present invention has a blooming period of late March until mid April and late August until frost. 'MNIHAR028' has a compact, uprightly rounded freely branching growth habit, and cold hardiness.

The new plant was first propagated via semi-hardwood cuttings in 2007 in Dearing, Ga. and has been asexually reproduced repeatedly by semi-hardwood cuttings in Dearing, Ga. for over 5 years, three generations. 'MNIHAR028' has been found to retain its distinctive characteristics through successive asexual propagations via semi-hardwood cuttings.

Plant Breeder's Rights for this variety have not been applied for. 'MNIHAR028' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, red colored flowers;
3. Numerous single flowers;
4. Easily propagated by semi-hardwood cuttings in late spring through summer;
5. Moderate growth rate under normal fertilization and moisture conditions;

6. Compact, uprightly rounded freely branching growth habit;
7. Grows well in containers;
8. Thrives in shade or sun; and
9. Hardy to Zone 7.

DESCRIPTION OF THE PHOTOGRAPHS

This new azalea hybrid variety is illustrated by the accompanying photographs. The colors shown are as true as can be reasonably obtained by conventional photographic means. The photographs are of four-year-old plants grown in filtered shade and full sun in 2009 and 2011 in Dearing, Ga.

DETAILED BOTANICAL DESCRIPTION OF THE NEW PLANT

Figure 1:
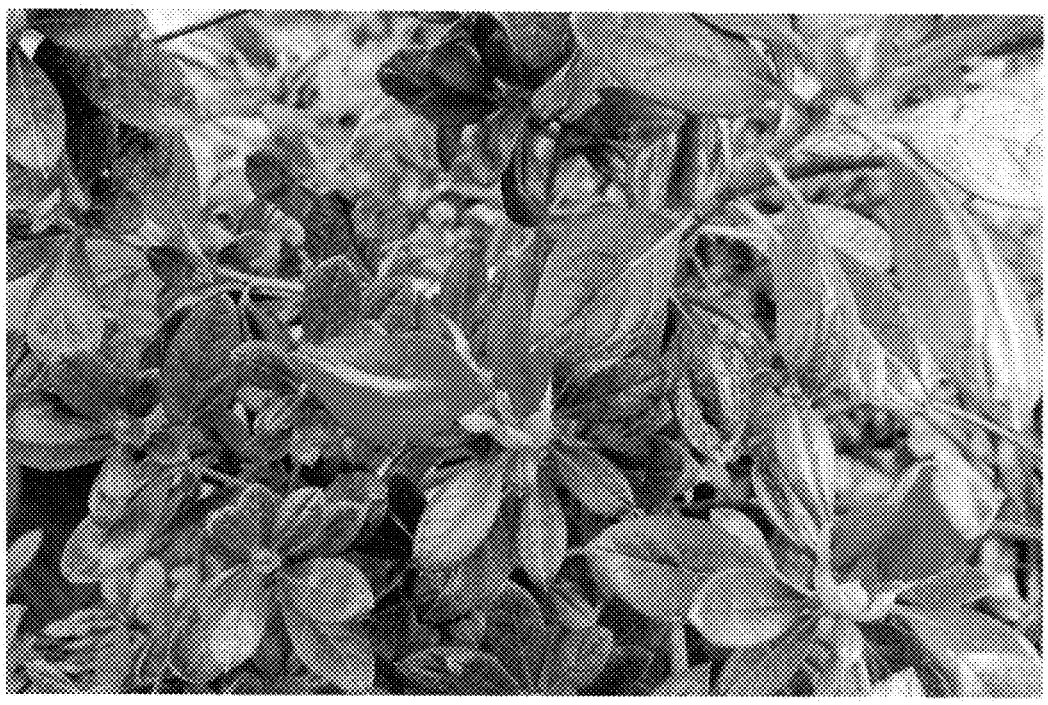
FIG. 1 shows a close-up of mature foliage and flower buds in September 2009.
Figure 2:
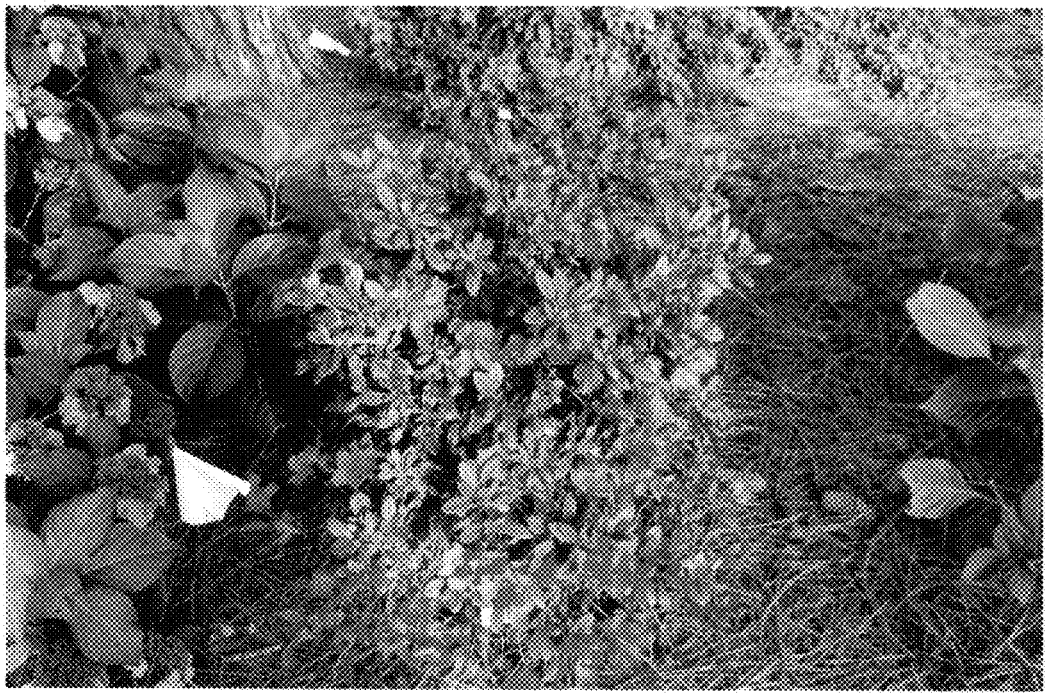
FIG. 2 shows mature foliage and growth habit and fall flowering.
Figure 3:
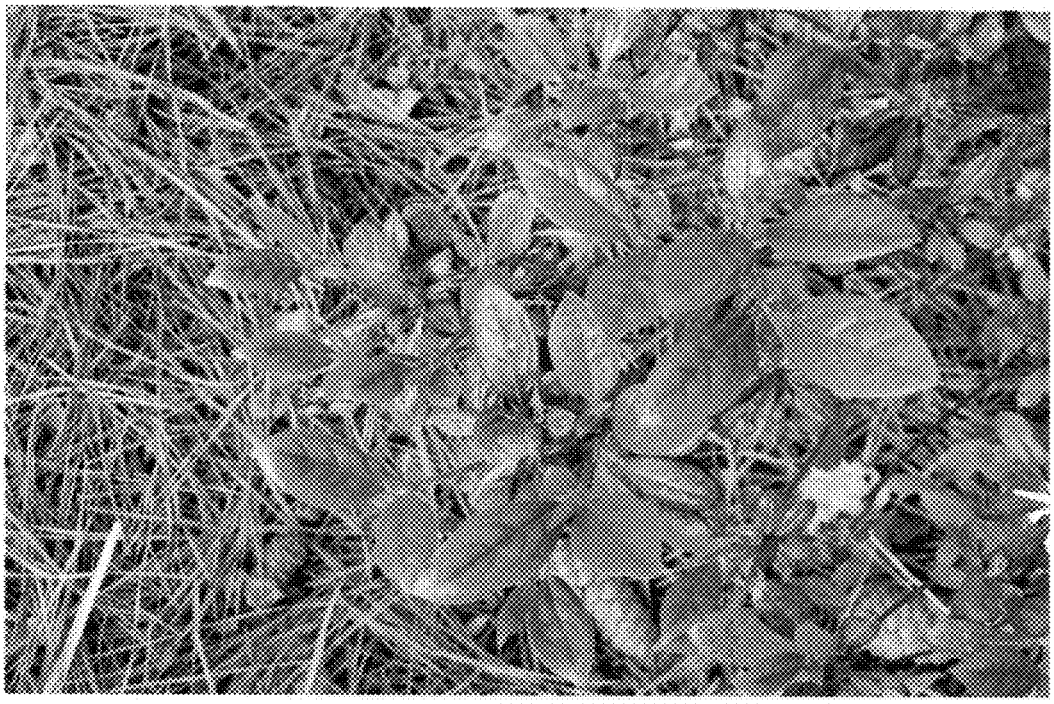
FIG. 3 shows a close-up of the flower buds and new growth in March 2011.
Figure 4:
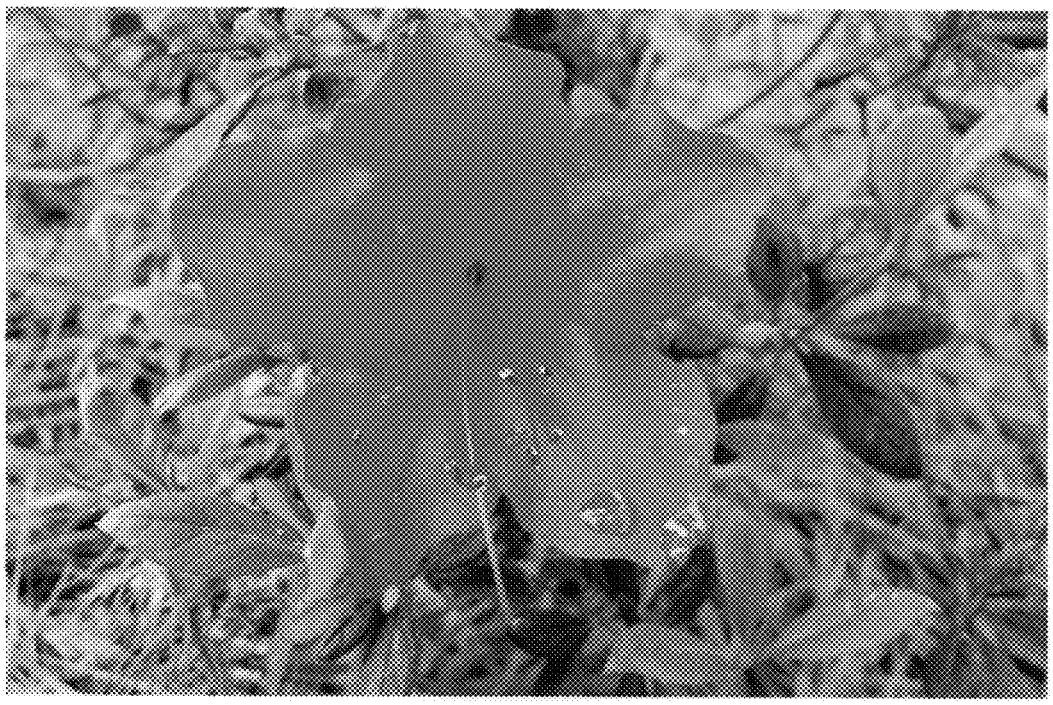
FIG. 4 shows a close-up of the flower size, form, and color in March 2009.

The following is a detailed description of the new azalea variety based on observations made of two and three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, 2010, 2011, and 2012. The colors of the various plant parts are detailed with reference to The Royal Horticultural Society Colour Chart (2001).

Classification:

*Family*.—Ericaceae.
*Species*.—*Rhododendron* sp.

*Common name*.—Azalea.
*Denomination*.—'MNIHAR028'.

Parentage:
*Female parent*.—Unknown.
*Male parent*.—Unknown.

Plant:
*Form*.—Compact, uprightly rounded.
*Texture*.—Medium.
*Height* (*at maturity*).—91.44 cm to 121.92 cm.
*Width* (*at maturity*).—121.92 cm to 152.4 cm.
*Growth habit*.—Freely branching; compact, uprightly rounded.
*Growth rate*.—Moderate growth rate under normal fertilization and moisture conditions. In a period of 6 years from a rooted cutting the plant reaches a height of 78.74 cm and a spread of 91.44 cm. The growth rate averages about 12.0 cm per year; the plant reaches a height of 91.44 cm to 121.92 cm at maturity while maintaining a compact, uprightly rounded habit due to the abundant deliquescent branch development.
*Spring growth*.—Beginning March 20$^{th}$, followed by continuous growth through fall.
*Life cycle*.—Perennial evergreen.

Leaves:
*Arrangement*.—Alternate, simple.
*Shape*.—Elliptic, oblliptical, and oblanceolate.
*Apex*.—Mucronate.
*Base*.—Acuminate.
*Margin*.—Entire.
*Length*.—6.0 cm.
*Width*.—2.2 cm.
*Venation pattern*.—Pinnate; the mid-veins and laterals are impressed on the upper surface and are prominent on the lower surface. Color (both upper and lower surface): RHS 146D (yellow-green).
*Immature leaf*.—Upper surface: Color: Semi-glossy to matte, RHS 137B (green). Pubescence: Strigose and scabrous. Color: RHS N155A (white) and RHS 164C (greyed-orange). Lower surface: Color: Matte, RHS 146B (yellow-green). Pubescence: Strigose and scabrous. Color: RHS N155A (white), RHS 157D (green-white), and RHS 159A (orange-white).
*Mature leaf*.—Upper surface: Color: Glossy, RHS N189A (greyed-green). Pubescence: Strigose. Color: RHS 164A (greyed-orange), RHS 164B (greyed-orange), and RHS 159A (orange-white). Lower surface: Color: Matte, RHS 147B (yellow-green). Pubescence: Strigose and scabrous. Color: RHS 164A (greyed-orange) and RHS 164B (greyed-orange).
*Petiole*.—Length: 0.95 cm. Diameter: 0.2 cm by 0.10 cm. Color: Immature: RHS 145A (yellow-green). Mature: RHS 146D (yellow-green). Pubescence: Strigose. Length: 0.15 cm. Color: Immature: RHS 155D (white). Mature: RHS 164A (greyed-orange).

Stems:
*Form*.—Branched at terminal buds with stems from auxiliary buds at leaf nodes.
*Young stems* (*actively growing, less than one year old*).—Color: RHS N144D (yellow-green). Pubescence: Strigose. Color: Begins RHS N155A (white) maturing to RHS 164A (greyed-orange). Length of fully elongated flush: Average 8.0 cm. Diameter: 0.2 cm.
*Mature stems* (*one year old and older*).—Color: RHS N144C (yellow-green), RHS N200C (grey-brown), and RHS N199C (grey-brown). Pubescence: Strigose, quantity decreases with age of the stem. Color: RHS 164A (greyed-orange). Length: 13.0 cm on average for full year's growth. Diameter: 0.3 cm in second year. Pith: Solid and uniform. Internode length: Average 1.5 cm on actively growing vegetative stems.

Flower buds:
*Arrangement and form* (*at terminal end*).—Borne in groups of two or three, sheathed by one to three modified leaf bracts.
*Bracts*.—Length: Average 1.6 cm. Width: 0.3 cm. Color: RHS 139A (green), RHS 146B (yellow-green), and RHS 145B (yellow-green).
*Shape*.—Ovate.
*Apex*.—Acute.
*Base*.—Rounded.
*Length* (*at tight bud*).—1.2 cm.
*Diameter* (*at tight bud*).—0.7 cm.
*Scales*.—Color: Immature: RHS 145C (yellow-green). Mature: RHS 144C (yellow-green). Length: 1.1 cm. Diameter: 0.45 cm. Texture: Matte; sericeous with some ciliate pubescence. Pubescence color: RHS 167C (greyed-orange).
*Pedicel*.—Length: 0.8 cm at point bud begins to open. Diameter: 0.2 cm. Color: RHS 145B (yellow-green) with slight RHS 50A (red) near the base of the calyx. Texture: Pubescent, villous and pilose pubescence. Pubescence color: RHS N155A (white) and RHS167C (greyed-orange).

Calyx:
*Diameter*.—0.6 cm from sepal apex to sepal apex.
*Color* (*both upper and lower surfaces*).—RHS 145B (yellow-green).
*Texture* (*both upper and lower surfaces*).—Pubescent, pilose, sericeous, and villous pubescence. Pubescence color: RHS N155A (white).
*Sepals*.—Length: 0.6 cm. Diameter: 0.4 cm. Quantity: 5.

Flowers:
*Type*.—Perfect, single flowers.
*Shape*.—Open funnel-shaped.
*Flowering habit and period*.—Borne on the current season's growth; three weeks beginning in late March thru mid April in Dearing, Ga.; flowering resumes late August and continues until frost which can be as late as November or December. Lastingness of flowers on the plant 3 to 5 days in the sun; 3 to 6 days in the shade.
*Fragrance*.—Absent.
*Persistence*.—Self-cleaning.
*Diameter*.—6.5 cm.
*Depth*.—4.0 cm.
*Inflorescence*.—Type: Solitary. Height: 4.8 cm. Diameter: 6.5 cm.
*Petals*.—Quantity per flower and arrangement: Five imbricate petals that are fused at the base and remain fused 2.0 cm to 3.0 cm from the base. Shape: Obovate. Apex: Rounded. Base: Fused. Margin: Entire, slightly undulate. Texture (both upper and lower surfaces): Glabrous. Length (petals without spots): 5.0 cm. Length (petals with spots): 5.3 cm. Width (petals without spots): 3.0 cm. Width (petals with spots): 32 cm. Color: Upper surface: RHS 45D (red); spots on the lower surface of the petal are RHS 53A (red). Lower surface: RHS 47B (red) and RHS 48B (red); spots on the lower surface of the petal are not visible.

Reproductive parts:

*Pistil*.—Quantity and form: Single, non-petaloid. Length: 5.3 cm. Diameter: 0.075 cm.

*Stigma*.—Color: RHS 185A (greyed-purple). Diameter: 0.15 cm.

*Style color*.—RHS 46A (red).

*Ovary*.—Pilose pubescence RHS N155A (white) with 5 locules. Color: RHS 141A (green).

*Stamens*.—Quantity: 5 per flower; non-petaloid. Length: Average 3.5 cm. Width: Average 0.05 cm. Color: RHS 48B (red).

*Anther*.—Length: 0.2 cm. Width: 0.1 cm. Color: RHS 187A (greyed-purple). Pollen: Abundant. Color: RHS 157A (green-white).

Fruit and seed: Observed.

*Maturity*.—The capsule matures in about 6 months in Dearing, Ga. and the fruit set is moderate and contains about 100 to 200 non-winged seeds.

*Capsule*.—Length: 1.0 cm. Width: 0.7 cm. Color: RHS 147B (yellow-green).

CULTURE

'MNIHAR028' grows well in a wide range of conditions and tolerates sun to shade. 'MNIHAR028' prefers moist, well-drained soil that is rich in organic matter and responds well to mulching and medium applications of fertilizer. 'MNIHAR028' does best in soil with a pH of 5.0 to 5.5 and is propagated with semi-hardwood cuttings in late spring through the summer. 'MNIHAR028' roots in five to six weeks with a high percentage of rooting (80% plus). Tissue culture is also an effective means of propagation of 'MNIHAR028'.

DISEASES AND INSECTS

Susceptible to lace bugs, root weevils, and spider mites. Fungal and bacterial pathogens have not been observed, but no resistance testing has been performed.

COMPARISON WITH COMMERCIAL VARIEITES

In Table 1, 'MNIHAR028' is compared to commercial varieties 'Conleb' (U.S. Plant Pat. No. 10,581) and 'Jay Valentine' (unpatented) which were used in the same hybridization program from which 'MNIHAR028' was developed.

TABLE 1

| Characteristic | 'MNIHAR028' | 'Conleb' | 'Jay Valentine' |
|---|---|---|---|
| Plant Height (Mature) | 91.44 cm to 121.92 cm | 121.92 cm to 152.4 cm | 121.92 cm |
| Flower Diameter | 6.5 cm | 6.5 cm | 6.25 cm to 7.62 cm |
| Flower Form | Single | Single to semi-double | Single |
| Flower Color | Red | Red | Deep Red |
| Bloom Period | Late March to mid April and late August until frost | April and late July until frost | April |
| Hardy Zone | 7 | 7 | 7 |
| Stamen Number | 5 | 0 to 9 | 5 |
| Stamen Type | Non-petaloid | Petaloid and non-petaloid | Petaloid |

When 'MNIHAR028' is compared to the commercial variety 'Roblen' (U.S. Plant Pat. No. 16,248), 'MNIHAR028' has a compact uprightly rounded growth habit with a height of 78.74 cm and a spread of 91.44 cm in 6 years, while 'Roblen' has a height of 91.44 cm and a spread of 60.96 cm in 6 years. Additionally, 'MNIHAR028' has single flowers with petals colored RHS 45D (red) on the upper surface and RHS 47B (red) on the lower surface, whereas 'Roblen' has single to semi-double flowers with petals colored RHS 44C (red).

I claim:

1. A new variety of azalea plant named 'MNIHAR028' as herein shown and described.

* * * * *